United States Patent [19]
Wise et al.

[11] Patent Number: 5,576,005
[45] Date of Patent: Nov. 19, 1996

[54] EFFECTIVENESS OF WART REMOVAL BY COMPOSITIONS INCLUDING PROPOLIS

[76] Inventors: Ronald D. Wise, 9037 Kildare Ave., Skokie, Ill. 60076; Predrag Konstantinovic, 376 Trinity La., Oakbrook, Ill. 60521

[21] Appl. No.: 495,219

[22] Filed: Jun. 27, 1995

[51] Int. Cl.$^6$ .................................................. A61K 35/78
[52] U.S. Cl. ........................... 424/401; 424/195.1
[58] Field of Search ..................... 424/401, 195.1, 424/404, 539; 514/846, 863, 887, 886, 871, 947, 828, 934

[56] References Cited

U.S. PATENT DOCUMENTS 4,880,630  11/1989  Novák ................................ 424/195.1

OTHER PUBLICATIONS

"Bee Propolis: The Ultimate Preventive Medicine?", *Bestways Magazine*; author and date unknown.
Brodell, R. T., and Bredle, D. L., "The Treatment of Palmar and Plantar Warts Using Natural Alpha Interferon and a Needleless Injector", *Dermatological Surgery*, 21:213–219 (1995).

Catalog from Beehive Botanicals, Hayward WI 54843.

Goodman and Gilman's *The Pharmacological Basis of Therapeutics*, McGraw–Hill, Inc., Eighth Edition 1993, p. 1587.

Label from Propolis Throat Spray; Gaia Herbs, Inc., Harvard, MA 01451.

Muhameaarov, G. Z., and Fedotov, R. F., "Propolis", *Bee and Human Health*, ed. Vinogradov and Zaitzev, published by Rosselhozizdat, Moscow, Russia (1966).

*Primary Examiner*—Thurman K. Page
*Assistant Examiner*—Sharon Howard
*Attorney, Agent, or Firm*—Brinks Hofer Gilson & Lione

[57] ABSTRACT

Compositions comprising propolis are effective in the treatment of warts. Compositions comprising propolis and salicylic acid either in combination or applied separately, are more effective at wart removal than is either component alone.

10 Claims, No Drawings

EFFECTIVENESS OF WART REMOVAL BY COMPOSITIONS INCLUDING PROPOLIS

BACKGROUND

Topical compositions including propolis show improved effectiveness over compositions such as salicylic acid for the treatment of warts.

Warts are a widespread medical problem that cause pain and discomfort, and may lead to complications if untreated or improperly treated. Warts are benign growths of the skin caused by a virus that involves the epidermis. Five different types of warts are classified by their clinical presentation. (1) *Verrucae vulgares* are common warts that display hyperkeratosis and may occur anywhere except the genital and mucous membranes and plantar surfaces (soles of the feet); (2) *Verrucae planae* are flat warts that usually occur on the face, trunk and extremities; (3) *Verrucae plantares* are warts that occur only on the soles of the feet; (4) *Condylomata acuminata* are venereal warts that occur on the genitals and mucous membranes; (5) premalignant warts (*Epidermoldysplasia verruciformis*) usually occur on the hands and feet and are rare in occurrence.

Currently, there are no completely successful, treatments for warts. Current treatments of verrucae involve physical destruction of the infected cells. Choice of treatment depends on the location, size, number, type of wart, age and co-operation of the patient. No one treatment modality is uniformally effective or directly antiviral.

Antiwart treatments include cryotherapy with liquid nitrogen, caustics and acids such as salicylic acid, lactic acid and trichloroacetic acid which destroy and peel off infected skin. Retinoic acid has been used topically to treat flat warts. Cantharidin is an extract of the green blister beetle that leads to blistering and focal destruction of the epidermis. Induction of allergic contact dermatitis with dinitrochlorobenzene (DNCB) produces local inflammation to warts on which this chemical has been applied.

Chemotherapeutic agents also employed for venereal warts include topically applied podophyllin resin which is more effective on mucosal surfaces. It is contraindicated in pregnancy and the potency of podophyllin preparations may be highly variable. Purified podophyllotoxin is available having activity that is reproducible in vitro Application of 5-fluorouracil is sometimes used to treat flat warts and *Condylomata acuminata*. Intralesional bleomycin has also been used but may cause extensive tissue necrosis.

Curettage, electrodesiccation, $CO_2$, and lasers are also used to treat warts. These treatment modalities are painful, require anesthesia and cause scarring. A new immunomodulator, Imiquimod has recently been used to topically treat genital and perianal warts and is currently under review by the Food and Drug Administration. The ultimate mechanism of this new composition is that it appears to act through the production of cytokines and activation of natural killer cells. According to a recent report, forty percent of the treated immunocompetent patients experienced resolution of their warts compared to the control group (treated with the vehicle alone). Three of sixteen patients who manifested no clinical evidences of warts after treatment developed a recurrence during a ten week follow up period. Subsequent studies of several hundred patients confirm the recurrence rates of 40 to 60%.

Salicylic acid in a topical composition is available for the treatment of warts. In this form, salicylic acid is a keratolytic agent that softens the hyperkeratotic areas by dissolving the intra-cellular matrix and enhancing shedding of scales. This composition is nonspecific, being also used for the treatment of psoriasis and other hyperkeratotic disorders. Unfortunately, application of salicylic acid is not always effective for wart resolution. Many patients with warts become frustrated while using salicylic acid because it is ineffective, forcing those patients to seek medical consultation. This may result in applying physical or surgical agents to alleviate patient distress.

Because no effective treatment for warts without appreciable side effects is yet available, other modalities are needed.

SUMMARY OF THE INVENTION

To address the need for an effective, topical wart treatment, a novel composition comprising propolis is provided for the treatment of warts. In particular, combining propolis with salicylic acid in a spreadable vehicle for topical application in treating warts, shows improved effectiveness over a current topical treatment, salicylic acid. The present invention relates to topical application of propolis compositions for successful treatment of the following types of warts: *Verrucae vulgares*, *Verrucae plantares*, *Condylomata acuminata* and *Verrucae planae*. Compositions used for the topical application include a combination of propolis and salicylic acid with a vehicle, and two separate compositions—one propolis, the other salicylic acid, applied sequentially to a wart but at about the same time. Either may be applied first, although the preferred sequence is that propolis is applied first to the wart, then salicylic acid is layered over it.

DETAILED DESCRIPTION OF THE PREFERRED EMBODIMENT

Compositions of propolis and salicylic acid are prepared in a pharmaceutical acceptable topical vehicle. Although the compositions comprising propolis can be used alone in the treatment of warts, combination with superficial cryo-surgery is also possible and desirable in some cases to decrease resolution time in the treatment. However, cryo-surgery is expensive and invasive. The combination of propolis and cryo-surgery produced faster therapeutic results compared to each modality alone.

Composition and Characteristics of Propolis

Propolis is a naturally occurring substance made by bees to cement defects in the hive and also to encapsulate insects and other animals that may invade the hive. The encapsulated organisms do not decay, possibly due to antimicrobial and antiviral properties of propolis.

Bees use propolis as a building and repair material. It is used to seal the cracks and irregularities in the hive nest, as well as for "embalming" the bodies of intruders, such as other insects, mice, frogs, snakes, and the like. Propolis (bee glue) is a resin, commonly of dark-green, brown, or dark-brown color. It is solid at 15° C. and becomes soft and pliable at 60°–70° C. Its specific gravity is 1.112–1.136. It has a melting temperature in the range of 80°–104° C., and it is soluble in alcohol, ether and some other solvents. The main components of propolis are plant tars, ether oils and wax, as well as bee saliva and pollen, iron and trace elements.

Propolis may be obtained from Beehives Botanicals, Wisconsin. The propolis purchased commercially is combined from various sources of beehives in North America. Propolis is generally combined with a solvent for use in the present invention. A suitable solvent is 95% ethyl alcohol which lowers the viscosity of propolis.

A suitable topical vehicle for salicylic acid in a combined or separate composition can include, e.g., white petroleum, mineral oil, Aquaphor®, Eucerin cream® and any other medium capable of containing the propolis in solution, suspension or emulsion, at all concentrations with salicylic acid suitable to produce an easily applied, "non-runny" composition and that will not cause damage to the skin. A preferred composition is 60–70% propolis, 15–20% salicylic acid, and 15–25% Aquaphor® as the vehicle (% are by weight/volume). An even more preferred composition is about 65% propolis, 17% salicylic acid, and 23% Aquaphor®. A composition that is less "runny" and more viscous is preferred.

Action of Propolis on Warts

Pharmacological actions of propolis are reported and may be due to the presence of large amounts of flavonoid (Pepeljnjak, 1985), particularly galangin and pinocembrine, together with a multitude of others. Flavonoids have a variety of pharmacological effects, some of which have been well studied (Havsteen, 1983).

The possibility exists that propolis acts as an antiviral agent that invades the infected epidermal cells and kills the virus within the cells. In the improved compositions of the present invention, the acidity of salicylic acid may facilitate entry of the propolis into the infected cell by disturbing the intercellular matrix of the wart, dissolving the protein and thus changing the physical-chemical properties of infected cell membranes. Entry of the propolis and/or the salicylic acid then produces a more effective antiviral therapy.

EXAMPLE 1

Treatment of Patients with Compositions Comprising Propolis

Fifty-three patients were treated with a composition comprising propolis. (Table 1) Every patient in the group failed to respond to previous therapeutic modalities that included salicylic acid alone, superficial liquid nitrogen cryosurgery, or a combination of the two.

The study included 53 patients. Twelve had *Condylomata acuminata*, 20 had *Verrucae vulgares*, one had *Verrucae planae*, 20 *Verrucae plantares*. Several had more than one type of wart: 1) two patients had *Verrucae vulgares* and *plantares*; 2) one had *Verrucae vulgares* and *Condylomata acuminata*, 3) one had *Verrucae plantares* and *Condylomata acuminata*, one had *Verrucae plantares* and *Condylomata acuminata*.

Initially a 10% solution in alcohol as the vehicle (wt. per volume) was used but this was later changed to a 65% (wt. per volume) solution. Generally, 95% ethyl alcohol is preferred. Both concentrations were well tolerated, but the 65% solution was preferred due to its higher viscosity and ease of application. It was thus easier to apply than the less concentrated solution which took more time to dry and dripped more than the 65% solution.

Fifty-three patients were treated with a composition of propolis in alcohol. In 35 of the 53 patients, the warts clinically cleared and were not seen on cutaneous examination. Eight (8) manifested a partial resolution in that the warts were found to have been reduced in bulk and quantity by at least 50%. Five (5) were lost to follow-up. Five showed no response, including the one patient with flat warts, but the warts in the latter patient were easily visualized and this led to efficient electrocautery therapy. Salicylic acid and cyrosurgery were not used with this patient because these modalities are not effective in the treatment of *Verrucae planae*. The average length of time of treatment was approximately four months.

Seven patients with plantar warts stated that although their warts were smaller within two months with the application of propolis solution, they desired an even faster therapeutic result. These patients were told to continue to apply the propolis twice daily. In addition these patients were given the prescription of 20% salicylic acid in Aquaphor® ointment to be applied over the propolis. All seven patients manifested complete clinical resolution by visual examination of the warts within two weeks thereafter. For 20% salicylic acid to be applied over the propolis a preferred routine is to apply twice daily.

A composition comprising propolis alone is an effective nonsurgical treatment of warts, because 36 patients out of 53 patients (67%) treated with propolis alone manifested complete resolution of their warts, that is, the warts were not clinically detected by visual examination. Patients treated with propolis alone manifested complete resolution of warts. Seven out of seven patients (100%) treated with the application of propolis and a salicylic acid mixture also manifested complete resolution and did so in approximately half the time as patients treated with propolis alone. A synergistic effect is supported. These patients were treated prior to propolis therapy with 20% salicylic acid Aquaphor® for at least two months and showed no clinical response to this therapeutic modality. Using the propolis with or without the salicylic acid led to a total of 43 out of 53 patients (81%) to manifest complete resolution, that is, the warts were not clinically detected by visual examination.

TABLE 1

Effect of Propolis on Warts

| Total patients with Condylomata Acuminata: 12 | |
|---|---|
| Sex | 12 males |
| Complete Resolution | 4 |
| No Resolution | 3 |
| Lost to follow up | 5 |
| Total patients with verrucae Vulgaris: 20 | |
| Sex | 11 males |
|  | 9 females |
| Complete Resolution | 19 |
| No Resolution | 1 |
| Total patients with verrucae Planae: 1 | |
| Sex | 1 female |
| Complete Resolution | 0 |
| No Resolution | 1 |
| Total patients with verrucae Plantares: 20 | |
| Sex | 12 males |
|  | 8 females |
| Complete Resolution | 7 males |
|  | 5 females |
| Partial Resolution | 5 males |
|  | 3 females |

The 7 males were treated with the application of 65% propolis in alcohol plus 20% salicylic acid in Aquaphor® twice daily Complete resolution is defined herein as warts not clinically detected by visual examination. Partial resolution is defined as warts that are reduced in bulk and quantity by at least 50% by visual examination.

EXAMPLE 2

Role of Flavonoids as Mechanism of Action of Propolis

It has been proposed that flavonoids are the active pharmacological agents in propolis. Yugoslavian researchers determined that the amount of two types of flavonoid: galangin and pinocembrine, was directly proportional to the effect of propolis on growth inhibition of *Bacillus subtilis* (Pepeljnjak, 1985). Flavonoids' pharmacological properties are discussed in an article by Havsteen (1983). It appears that flavonoids have a variety of effects on the human body. For example, they produce an anti-inflammatory effect by suppressing prostaglandin synthesis, they block histamine release by suppressing $H^+$-ATPase of mast cells, they relieve local pain by suppressing prostaglandin synthesis, and they even normalize cancer cells in cell culture, presumably by affecting the (Na-K)ATPase pump. Flavonoids have also been shown to have an antiviral effect by suppressing $H^+$-ATPase of lysosomal membranes and preventing the lysis of the viral protein coat necessary for entry of the virus into a cell.

Flavonoids have been shown to have extremely low toxicity in animals. For rats, the $LD_{50}$ is 2–10 g per animal for most flavonoids. Similar doses in humans are quite unrealistic (Havsteen, 1983).

Viral infection remains completely harmless until the protein coat surrounding the nucleic acid has been removed by lysosomal digestion. This process requires fusion of the viral mantle with the lysosomal membrane, which must be aided by a proton ATPase and possibly by phospholipase $A_2$. The former enzyme presumably activates the cathepsins by importing protons, which may weaken the lysosomal membrane. Both of these enzymes are inhibited by flavonoid and similar compounds. Therefore, propolis may inhibit viral penetration of the cells and thereby stop or slow the infection process.

EXAMPLE 3

Treatment of Warts with Propolis and Salicylic Acid

Propolis is prepared in 95% ethyl alcohol at a 65% wt volume. Salicylic acid is prepared in Aquaphor® at a 20% wt/volume. The propolis composition is applied to the surface of a wart. An amount sufficient to cover the wart is applied (about ½ mg of propolis/cm²).

In a short interval, the salicylic acid composition is applied in similar fashion. The entire procedure is repeated 1–2 times a day until the wart resolves.

The compositions are generally applied 1–2 times a day on each wart. The surface of the wart is covered with the compositions. An effective amount is of the order of ½ mg/cm² of wart surface area, although other amounts are within the scope of the present invention. Amounts are adjusted based on size of the wart and response therapy.

DOCUMENTS CITED

Haysteen, B. (1983) "Flavonoid, a class of natural products of high pharmacological potency." *Biochemical Pharmacology* 32: 1141–1148.

Morfei, A. et al. (1980) "Investigations concerning the action of several chemical and biological agents in HBsAg." *Rev. Roum. Med.—Virol.* 31: 273–278.

Pepeljnjak, S., et al. (1985) "Flavonoid content in propolis extracts and growth inhibition of *Bacillus subtilis.*" *Pharmazie* 40: 112–123.

Pepeljnjak, S. et al. (1982), "Inhibition of growth and biosynthesis of ochratoxin A in *Aspergillus sulfureous* NRRL 4077 by propolis extract." *Pharmazie* 37: 439–440.

We claim:

1. A composition for the topical treatment of warts comprising an amount of propolis and salicylic acid, said amount effective in the treatment of warts, in a pharmacologically accepted topical vehicle, wherein said vehicle is a medium capable of containing the propolis in solution, suspension or emulsion.

2. The composition of claim 1, wherein the ratio of propolis to salicylic acid is approximately 65% to 17%.

3. The composition of claim 1, wherein said vehicle is selected from the group consisting of white petroleum, mineral oil and a medium capable of containing the propolis in solution, suspension or emulsion.

4. A composition for the topical treatment of warts comprising an amount of propolis, said amount effective in the treatment of warts in a pharmaceutically acceptable topical vehicle, wherein said vehicle is a medium capable of containing the propolis in solution, suspension or emulsion.

5. The composition of claim 4, wherein said vehicle comprises ethyl alcohol.

6. A method for the topical treatment of warts, said method comprising applying an amount of the composition of claim 1, said amount effective in the treatment of warts to an area of skin having warts.

7. A method for the topical treatment of warts, said method comprising applying an amount of a composition of claim 4, said amount effective in the treatment of warts to an area of skin having warts.

8. A combined topical treatment for warts wherein a separate application of propolis is accompanied by application of salicylic acid in a pharmacologically acceptable topical vehicle.

9. A method for the topical treatment of warts, said method comprising application of an amount of the composition of claim 1 effective for the treatment of warts to an area of skin having warts, wherein said treatment comprises topical application of said composition in a concentration of about 0.5 mg of the composition per square centimeter of wart surface area, said application being done at least once per day.

10. A method for the topical treatment of warts, said method comprising application of an amount of the composition of claim 4 effective for the treatment of warts to an area of skin having warts, wherein said treatment comprises topical application of said composition in a concentration of about 0.5 mg of the composition per square centimeter of wart surface area, said application being done at least once per day.

* * * * *